(12) United States Patent
Vishwakarma et al.

(10) Patent No.: US 9,868,695 B2
(45) Date of Patent: Jan. 16, 2018

(54) 10-SUBSTITUTED COLCHICINOIDS AS POTENT ANTICANCER AGENTS

(71) Applicant: Council of Scientific & Industrial Research, New Delhi (IN)

(72) Inventors: Ram A. Vishwakarma, Jammu (IN); Sandip B. Bharate, Jammu (IN); Ajay Kumar, Jammu (IN); Baljinder Singh, Jammu (IN); Ashok Kumar, Jammu (IN); Shashi Bhushan, Jammu (IN); Abid Hamid, Jammu (IN); Prashant Joshi, Jammu (IN); Santosh K. Guru, Jammu (IN); Suresh Kumar, Jammu (IN); Aashiq Hussain, Jammu (IN); Asif K. Qazi, Jammu (IN); Sonali S. Bharate, Jammu (IN); Parduman Sharma, Jammu (IN); Ajit K. Saxena, Jammu (IN); Dilip M. Mondhe, Jammu (IN); Girish Mahajan, Jammu (IN); Zahoor Wani, Jammu (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/519,054

(22) PCT Filed: Oct. 14, 2015

(86) PCT No.: PCT/IN2015/050135
§ 371 (c)(1),
(2) Date: Apr. 13, 2017

(87) PCT Pub. No.: WO2016/059650
PCT Pub. Date: Apr. 21, 2016

(65) Prior Publication Data
US 2017/0226051 A1 Aug. 10, 2017

(30) Foreign Application Priority Data
Oct. 14, 2014 (IN) .......................... 2929/DEL/2014

(51) Int. Cl.
C07C 233/41 (2006.01)
C07C 231/12 (2006.01)
A61K 31/165 (2006.01)

(52) U.S. Cl.
CPC .......... *C07C 233/41* (2013.01); *A61K 31/165* (2013.01); *C07C 231/12* (2013.01); *C07C 2603/34* (2017.05)

(58) Field of Classification Search
None
See application file for complete search history.

(56) References Cited

FOREIGN PATENT DOCUMENTS

WO WO-2011/091114 A2 7/2011

OTHER PUBLICATIONS

International Search Report, issued in PCT/IN2015/050135, dated Feb. 12, 2016.
S-K. Kim et al., "The colchicine derivative CT20126 shows a novel microtube-modulating activity with apoptosis," Experimental & Molecular Medicine 45, pp. 1-7, (2013).
B. Singh et al. "Colchicine derivatives with potent anticancer activity and reduced P-glycoprotein induction liability," Organic & Biomolecular Chemistry 13, 5674-5689, (2015).

*Primary Examiner* — Samantha Shterengarts
(74) *Attorney, Agent, or Firm* — Locke Lord LLP; Nicholas J. DiCeglie, Jr.

(57) ABSTRACT

The present invention relates to the compounds of formula I wherein R is as herein described. The present invention particularly relates to synthesis and antiproliferative activity of 10-substituted colchicinoids. Compounds of the invention can be used for prevention or in the treatment of cancer disease.

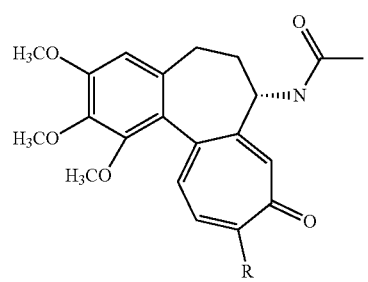

7 Claims, 3 Drawing Sheets

10-SUBSTITUTED COLCHICINOIDS AS POTENT ANTICANCER AGENTS

CROSS REFERENCE TO RELATED APPLICATIONS

This application is a 371 U.S. National Phase Application of PCT/IN2015/050135, filed Oct. 14, 2015, which claims priority to Indian Patent Application No. 2929/DEL/2014, filed Oct. 14, 2014, the disclosures of each of which are expressly incorporated herein by reference in their entireties.

FIELD OF THE INVENTION

The present invention relates to 10-substituted colchicinoids for treatment of cancer diseases. The present invention particularly relates to synthesis and anticancer activity of 10-substituted colchicinoids. Compounds of the invention are devoid of P-gp induction liability which is associated with colchicine.

BACKGROUND OF THE INVENTION

Colchicine (1), a natural product isolated from *Colchicum autumnale* (Meadow Saffron) has been used for the treatment of rheumatic condition 'gout' and also for the treatment of familial Mediterranean fever, pericarditis, and Behcet's disease (Cocco G. et al., *Eur. J. Intern. Med.* 2010, 21, 503-508; Niel E. et al., *Joint Bone Spine* 2006, 73, 672-678; Terkeltaub, R. A., *Semin. Arthritis Rheum.* 2009, 38, 411-419). Colchicine exhibits potent anticancer activity by binding to tubulin, inhibiting its self-assembly and microtubule polymerization and finally arresting cell division at metaphase. Colchicine interacts mainly with three proteins viz. tubulin, cytochrome P4503A4 (CYP3A4), and P-glycoprotein (P-gp). CYP3A4 is the major protein found mainly in liver and intestine which metabolizes colchicine by demethylating the —OMe groups at C-2 and C-3 positions. The development of tumor resistance to colchicine mainly occurs via its P-gp substrate and induction activity, and increase in the expression of βIII tubulin isotype (Niel E. et al., *Joint Bone Spine* 2006, 73, 672-678; Druley T. E. et al., *Biochemistry* 2001, 40, 4323-4331; Tateishi T. et al., *Biochem. Pharmacol.* 1997, 53, 111-116).

The P-gp induction is responsible for the multidrug resistance particularly in the case of cancer cells and makes the currently available chemotherapy ineffective (Ling V., *Cancer Chemother. Pharmacol.* 1997, 40, S3-S8; Aller S. et al., *Science* 2009, 323, 1718-1722). Therefore, the search for cytotoxic compounds which are devoid of multidrug resistance is of great importance (Lage H., *Cell. Mol. Life Sci.* 2008, 65, 3145-3167). Colchicine (1) is a substrate of P-gp efflux pump and it induces its activity by inducing conformational change (Druley T. E. et al., *Biochemistry* 2001, 40, 4323-4331). To overcome the P-gp mediated resistance of colchicine, Cosentino et al. demonstrated that its N-benzylated derivative (2) showed no loss in cytotoxic activity in the resistant A2780AD ovarian carcinoma cells which are known to overexpress the ABCB1 drug transporter (Cosentino L., *J. Med. Chem.* 2012, 55, 11062-11066).

Several patents have been published related to colchicine and their compounds for the treatment of inflammatory diseases, antiproliferative, gout, anti-tumor, etc. Thorson et al. have synthesized series of neoglycosides of colchicine with cytotoxic activity (U.S. Pat. No. 8,232,254). Nielsen et al. (US20110184061), Nielsen et al. (WO2011091114) and Bombardelli et al. (WO1996011184) have designed thiocolchicine and colchicine derivatives suitable for use as a muscle relaxant, an anti-inflammatory agent, as an anti-gout agent, as an anti-proliferative agent, or as an anti-cancer agent. Tuszynski et al. (US20120225912), Brown et al. (WO2002056872) and Alberta health services (WO2011022805) have synthesized and patented colchicine derivatives for targeting cancer diseases. Han et al. have patented several colchicine derivatives for immunomodulatory action (US20130011417). Colchicine is also patented for control of retroviruses by The Rockefeller University USA (WO1989012444). Fringuelli et al. have synthesized and patented colchicine derivatives for the antifibrotic treatment of chronic hepatic diseases (WO2008102397). Mutual Pharmaceutical Company, Philadelphia, USA have used colchicine and macrolide antibiotics to inhibit P-glycoprotein in order to enhance the effect of colchicine. To the best of our knowledge, there is no patent where the P-glycoprotein induction liability of colchicine scaffold has been reduced by the structural modification of colchicine (U.S. Pat. No. 7,935,731).

Recent report on the discovery of 3D-structure of P-gp from *Caenorhabditis elegans*, encouraged us to use 3D-crystal structure of P-gp to design colchicine derivatives for addressing its issue of P-gp induction liability (Jin M. S., *Nature* 2012, 490, 566-569). The structure-activity relationship (SAR) of colchicine as anti-tubulin agent (Cosentino L., *J. Med. Chem.* 2012, 55, 11062-11066; Andreu J., *Biochemistry* 1982, 21, 6465-6476; Das L., *Biochemistry* 2005, 44, 3249-3258; Cifuentes M., *Bioorg. Med. Chem. Lett.* 2006, 16, 2761-2764; Zefirova O. N., *Bioorg. Med. Chem.* 2011, 19, 5529-5538; Nakagawa G. K., *Bioorg. Med. Chem. Lett.*

2005, 15, 235-238; Boyer F. D., *Bioorg. Chem.* 2010, 38, 149-158; Chen J., *Mini Rev. Med. Chem.* 2009, 9, 1174-1190) is available in the literature, however its SAR for P-gp induction activity has not been examined. The limitation of colchicine in the treatment of cancer is due to its P-gp liability. The present invention reports discovery of 10-substituted colchicinoids with better in vitro and in vivo anticancer activity than colchicine, and with reduced P-gp induction liability.

Objectives of the Invention

The main object of the invention is to provide better anticancer compounds devoid of P-glycoprotein induction liability.

Another objective of the present invention is to provide 10-substituted colchicinoids.

Yet another objective is to provide less toxic compounds than colchicine.

SUMMARY OF THE INVENTION

Accordingly, the present invention provides a compound represented by the formula I thereof,

I wherein, R groups is selected from the group consisting of Piperazine, Piperazine carboxylate, 4-Amino piperidine, 4-Aryl piperidine, Prolinol, β-Carboline, or 4-chloro-3-(Trifluoromethyl)phenylamine.

In one embodiment, the compound is selected from the following formulae:

1a

1b

1c

1d

In a second aspect of the invention, a method is presented for treating or preventing P-gp-mediated multi-drug resistant cancer disease by identifying a patient suffering from or at a risk of developing a cancer disease and administering to the patient a therapeutically-effective amount of a compound represented by the formula I.

wherein, R group is selected from Piperazine, Piperazine carboxylate, 4-Amino piperidine, 4-Aryl piperidine, Prolinol, β-carboline, or 4-chloro-3-(Trifluoromethyl)phenylamine.

Another aspects of the invention is a process for the preparation of compound of formula I, wherein the compound is prepared by reacting colchicine (1) in polar organic solvent with a corresponding amine in the ratio in the range of 1:4 under stirring at room temperature for 24-72 hours and purification by conventional method to obtain compound of formula I.

Another embodiment of the invention is the polar organic solvent selected from the group consisting of methanol, acetone, ethanol, dimethyl sulfoxide, ethyl acetate, dimethylformamide.

In yet another embodiment of the invention the temperature is preferably in the range of 25-40° C.

In further embodiment the time period is preferably 60-70 hours.

Yet another embodiment of the invention is to provide 10-substituted colchicinoid for use in treatment of P-gp mediated multi-drug resistant cancer.

In one embodiment, the patient is human.

In another embodiment of the invention the said compounds are useful for the treatment of P-gp mediated multidrug resistant cancer.

DETAILED DESCRIPTION OF THE INVENTION

Colchicine (1) is a substrate and inducer of P-glycoprotein. The present invention reports compounds, represented by general structure I, possessing better in vitro and in vivo anticancer activity and with reduced P-gp induction liability.

I

Figure 1:
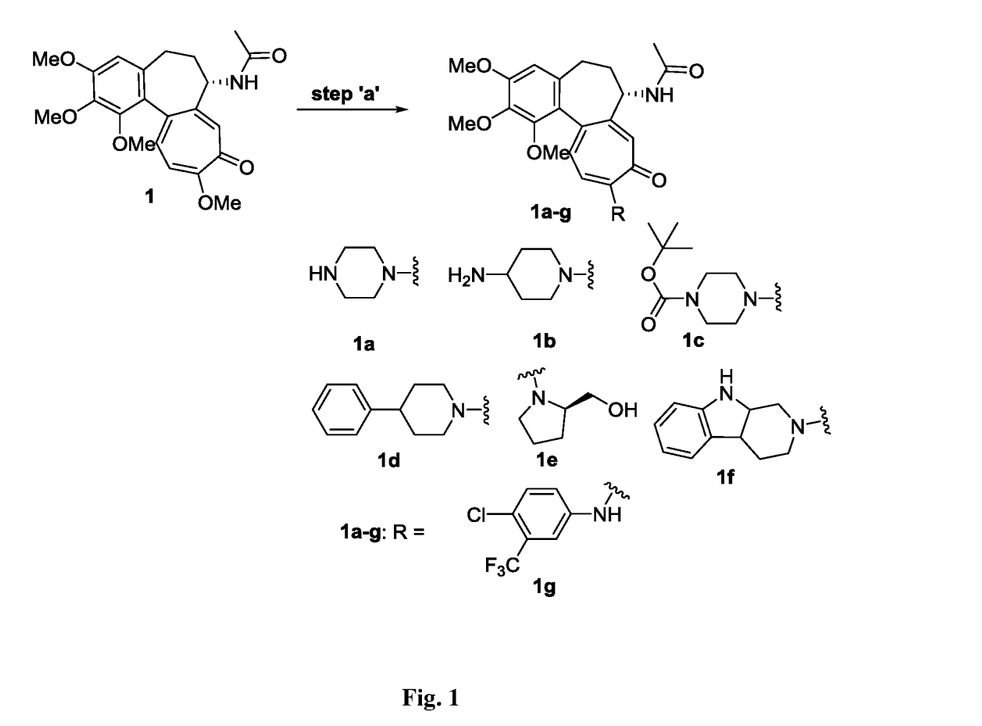
FIG. 1 is a scheme illustrating the chemical synthesis of compounds claimed in the invention. Reagents and conditions: (a) amine (1.0 mmol), MeOH (3 mL), rt, 24-72 h, 60-90%.
Figure 2:
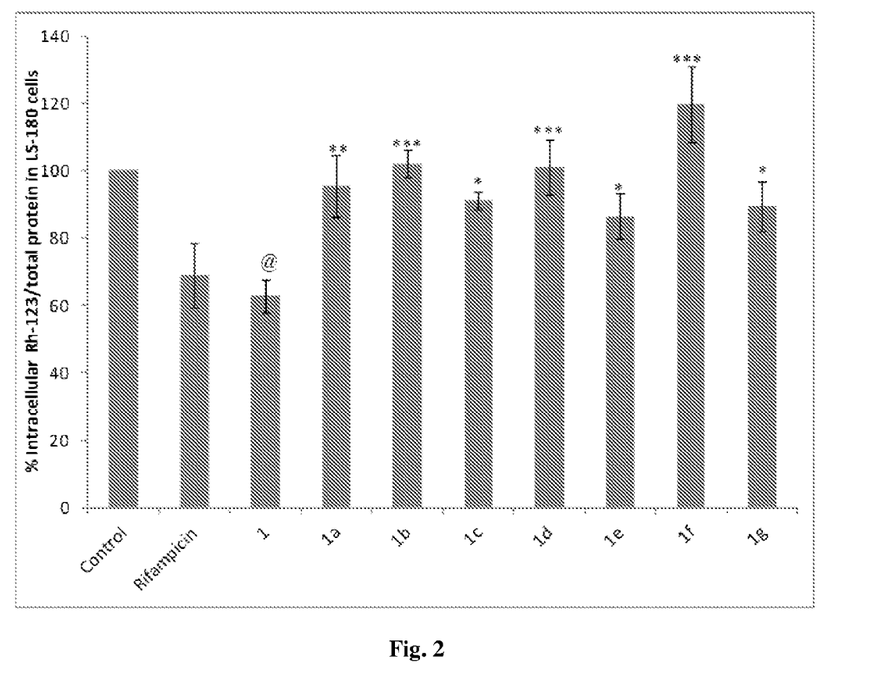
FIG. 2 is a scheme illustrating the P-gp activity of colchicine (1) and compounds (1a-1g) at 100 nM, measured in terms of the % intracellular accumulation of Rhodamine 123/total protein inside LS180 cells. The decrease in the % intracellular accumulation (compared to control) of Rh123 indicates induction of P-gp. Rifampicin (10 μM) was used as a reference P-gp inducer. Statistical comparisons were made between control vs 1 and 1 vs other compounds. The p value<0.5 was considered to be significant. P value *<0.5, <0.01, *<0.001. Comparison between control and 1 are represented by @.

A series of 10-substituted compounds were prepared using scheme depicted in FIG. 1. Treatment of colchicine (1) with different amines in methanol produced corresponding 10-amino-linked compounds 1a-g in 60-81% yield. Colchicine (1) along with all synthesized compounds were screened for their ability to induce P-gp in P-gp overexpressing LS-180 cells (ECACC type, purchased from Sigma, Cat. no. 87021202, cell passage no. 52) using rhodamine123 (Rh123) cell exclusion method. The rifampicin (69% intracellular accumulation of Rh123) was used as positive control in this study. Results are depicted in FIG. 2. Colchicine showed potent P-gp induction activity as indicated by the decrease in % intracellular accumulation of Rh123 in LS180 cells (62%) compared to the control (100%). However, synthesized compounds displayed significantly reduced P-gp induction activity; which comprises of compounds substituted with Piperazine 1a, 4-Amino piperidine 1b, 4-Phenyl piperidine 1d, Tryptoline 1f, 4-Chloro-3-(trifluoromethyl)aniline 1g all showing 90% intracellular accumulation of Rh123 in LS180 cells compared to the control (100%) (FIG. 2). Further, the $EC_{50}$ values of selected compounds 1d and 1g along with colchicine (1) was calculated for P-gp induction activity. The derivative 1d and 1g showed higher $EC_{50}$ value compared to colchicine (1). These results suggest that synthesized compounds are less liable to P-gp induction compared to colchicine (1) (Table 1).

The in vitro antiproliferative activity of compounds 1a-1g along with colchicine (1) was determined by MTT assay in two different cancer cell lines viz. HCT-116 (NCI, passage no. 5) and Colo-205 (National Cancer Institute; U.S) 116 (NCI, passage no. 3). The results are summarized in Table 2. The 10-amino substituted compound 1g displayed promising antiproliferative activity in both cell lines (HCT-116, Colo-205) with $IC_{50}$ values of 0.040 and 0.030 µM, respectively. The compound 1g showed better antiproliferative activity compared to natural product colchicine. The compounds exhibiting promising cytotoxicity in HCT-116 cells ($IC_{50} \leq 1$ µM) along with complete loss of P-gp induction activity include 1g, and 1d.

Figure 3:
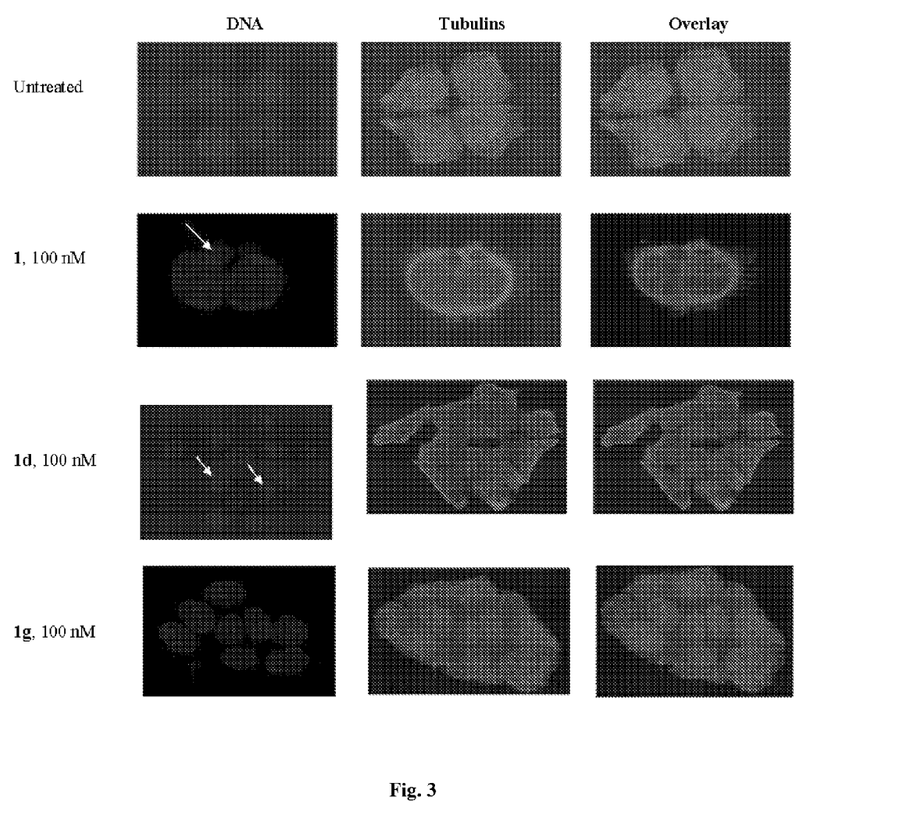
FIG. 3 is a diagram illustrating effect of colchicine (1) and compounds 1d and 1g on microtubules in HCT-116 cells (National Cancer Institute; U.S). Cells were cultured on coverslips. After 24 h, the cells were treated with 100 nM of compound. Immunocytochemical staining was conducted using anti-α-tubulin antibody and Alexa Flour-488-labeled secondary antibody. Nuclei were stained with DAPI (left panel). The data are representative of three separate sets of experiments.

The promising candidates identified through P-gp screening and antiproliferative screening were further studied for tubulin polymerization inhibition activity. Colchicine (1), 10-amino linked derivative 1d and 1g were tested for their ability to show disruption of microtubule assembly using confocal microscopy. As shown in FIG. 3, the cells treated with colchicine (1), derivative 1d and 1g showed a remarkable disruption and loss of microtubules compared to the control.

The solubility of colchicine (1) and best compounds 1d and 1g were determined in biological media's such as phosphate buffer saline (PBS), simulated gastric fluid (SGF), and simulated intestinal fluid (SIF). Results are shown in Table 3.

Further, the compound 1g was evaluated for pharmacokinetic studies. The pharmacokinetics of 1g was evaluated in BALB/c mice following a single 10 mg/Kg dose administration by oral route and 1.0 mg/Kg dose administration by IV route. Following oral administration, elimination half life $(t_{1/2,\beta})$ was found to be 5.43 h and $AUC_{0-t}$ was found to be 16899 ng·h/mL. Following IV administration, elimination half life $(t_{1/2,\beta})$ was found to be 2.78 h and clearance was ~6 mL/min/Kg. The absolute oral bioavailability was 64%. The pharmacokinetic parameters are summarized in Table 4 and 5. The PK results indicated excellent plasma exposure of the compound 1g and thus we decided to investigate the effect of this compound in in vivo anticancer model.

The compound 1g along with colchicine (1) was evaluated for their ability to reduce tumor in Ehrlich solid tumor model in mice. The results are summarized in Table 6. The compound 1g has shown promising activity at 1 mg/kg dose with 47.35% inhibition in tumor size compared to control. There is no mortality observed in the group treated with 1g. On the other hand, colchicine (1) has shown promising activity with 52.29% inhibition at 0.75 mg/kg dose but the mortality was observed in 2 animals in the group of 7 animals. However, colchicine (1) has shown toxicity at 1 mg/kg with mortality of 5 animals in the group of 7 animals. 5-Fluorouracil was used as positive control with 54.78% inhibition at dose 22 mg/kg. These results clearly indicate that our compound 1g has better safety profile compared to colchicine.

A class of 10-substituted colchicinoids is presented and defined by structural formula I:

I wherein, R group is selected from Piperazine, Piperazine carboxylate, 4-Amino piperidine, 4-Aryl piperidine, Prolinol, β-carboline, or 4-chloro-3-(Trifluoromethyl)phenylamine.

Compounds of the invention derived from Formula I include, but are not limited to, the following chemical structures:

(1a)

N-[(7S)-1,2,3-Trimethoxy-9-oxo-10-(piperazin-1-yl)-5,6,7,9-tetrahydrobenzo[a]heptalen-7-yl]acetamide (1b)

N-[(7S)-1,2,3-Trimethoxy-9-oxo-10-(4-amino-piperidin-1-yl)-5,6,7,9-tetrahydrobenzo[a]heptalen-7-yl]acetamide (1c)

N-[(7S)-1,2,3-Trimethoxy-9-oxo-10-(N-boc-piperazin-1-yl)-5,6,7,9-tetrahydrobenzo[a]heptalen-7-yl]acetamide (1d)

N-[(7S)-1,2,3-Trimethoxy-9-oxo-10-(4-phenyl-piperidin-1-yl)-5,6,7,9-tetrahydrobenzo[a]heptalen-7-yl]acetamide (1e)

N-[(7S)-1,2,3-Trimethoxy-9-oxo-10-(L-prolinol-1-yl)-5,6,7,9-tetrahydrobenzo[a]heptalen-7-yl]acetamide (1f)

N-[(7S)-1,2,3-Trimethoxy-9-oxo-10-(2,3,4,9-tetrahydro-1H-pyrido[3,4-b]indole-2-yl)-5,6,7,9-tetrahydrobenzo[a]heptalen-7-yl]acetamide N-[(7S)-1,2,3-Trimethoxy-9-oxo-10-[3-(trifluoromethyl)-4-chloro-phenylamino]-5,6,7,9-tetrahydrobenzo[a]heptalen-7-yl]acetamide The compounds of the invention can be used to treat a patient (e.g. a human) that suffers from or is at a risk of suffering from a disease, disorder, condition, or symptom described herein. The compounds of the invention can be used alone or in combination with suitable excipients in methods of treating or preventing P-gp mediated multidrug resistance cancer disease. Each such treatment described above includes the step of administering to a patient in need thereof a therapeutically effective amount of the compound of the invention described herein to delay, reduce or prevent such a disease, disorder, condition, or symptom. The compounds of the invention presented herein may be also useful in efflux of toxins out of the body.

It is understood that the foregoing examples are merely illustrative of the present invention. Certain modifications of the articles and/or methods employed may be made and still achieve the objectives of the invention. Such modifications are contemplated as within the scope of the claimed invention.

EXAMPLES

Following examples are given by way of illustration and should not construed the scope of present invention.

Example 1: Synthesis of N-[(7S)-1,2,3-Trimethoxy-9-oxo-10-(piperazin-1-yl)-5,6,7,9-tetrahydrobenzo[a]heptalen-7-yl]acetamide (1a)

To the solution of colchicine (1, 0.25 mmol) in MeOH (3 mL) was added corresponding amine (Piperazine, 1.0 mmol). The reaction mixture was stirred at room temperature for 24-72 h, and then the mixture was diluted with cold water and extracted with ethyl acetate followed by purification with silica gel column chromatography (MeOH:CHCl$_3$) to yield compounds 1a (67% yield); yellow solid; mp 158-161° C. $^1$H NMR (CDCl$_3$, 400 MHz): δ 7.44 (1H, s, br, NH), 7.28 (1H, s, C8-H), 7.25 (1H, d, J=10.8 Hz, C12-H), 6.79 (1H, d, J=10.8 Hz, C11-H), 6.52 (1H, s, C4-H), 4.64-4.61 (1H, m, C7-H), 3.93 (3H, s, Ar—OCH$_3$), 3.89 (3H, s, Ar—OCH$_3$), 3.64 (3H, s, Ar—OCH$_3$), 3.56-3.53 (2H, m, C2'-Ha, C6'-Ha), 3.35-3.32 (2H, m, C2'-Hb, C6'-Hb), 3.14-3.04 (4H, m, C3'-H, C5'-H), 2.50-2.39 (2H, m, C5-Ha, C6-Ha), 2.25-2.18 (1H, m, C5-Hb), 2.01 (3H, s, C14-CH$_3$), 1.87-1.85 (1H, m, C6-Hb); $^{13}$C NMR (CDCl$_3$, 125 MHz): δ 181.35 (C9), 169.78 (C13), 158.35 (C10), 153.15 (C3), 151.29 (C1), 149.63 (C7a), 141.57 (C2), 136.11 (C12), 134.36 (C12a), 134.27 (C4a), 129.22 (C8), 125.96 (C12b), 118.26 (C11), 107.29 (C4), 61.46 (C1-OCH$_3$), 61.41 (C2-OCH$_3$), 56.09 (C3-OCH$_3$), 51.87 (C7), 49.74 (C2'), 49.74 (C6'), 45.85 (C3'), 45.85 (C5'), 36.99 (C6), 30.05 (C5), 23.03 (C14); HR-MS: m/z calcd 454.2317 for C$_{25}$H$_{31}$N$_3$O$_5$+H$^+$ (454.2336); IR (CHCl$_3$): ν$_{max}$ 3283, 2926, 2852, 1660, 1544, 1462, 1349, 1234, 1195, 1118, 1033 cm$^{-1}$.

Example 2: Synthesis of N-[(7S)-1,2,3-Trimethoxy-9-oxo-10-(4-amino-piperidin-1-yl)-5,6,7,9-tetrahydrobenzo[a]heptalen-7-yl]acetamide (1b)

Procedure for synthesis of 1b is similar to example 1 except corresponding amine (4-Amino-piperidine). Yield, 73%; yellow solid; mp 154-155° C. $^1$H NMR (CDCl$_3$, 400 MHz): δ 7.40 (1H, d, J=11.6 Hz, C12-H), 7.39 (1H, s, C8-H), 7.22 (1H, d, J=8 Hz, NH), 6.63 (1H, d, J=11.6 Hz, C11-H), 6.51 (1H, s, C4-H), 4.64-4.61 (1H, m, C7-H), 3.92 (3H, s, Ar—OCH$_3$), 3.88 (3H, s, Ar—OCH$_3$), 3.60 (3H, s, Ar—OCH$_3$), 3.08-3.03 (4H, m, C2'-H, C6'-H), 2.81-2.70 (1H, m, C2'-H), 2.68-2.55 (1H, m, C4'-H), 2.48-2.35 (2H, m, C6-Ha, C5-Ha), 2.26-2.18 (1H, m, C6-Hb), 2.01 (3H, s, C14-CH$_3$), 1.89-1.84 (1H, m, C5-Hb), 1.74-1.70 (4H, m, C3'-H, C5'-H); $^{13}$C NMR (CDCl$_3$, 125 MHz): δ 175.08 (C9), 169.90 (C13), 153.01 (C10), 152.84 (C3), 151.06 (C1), 150.08 (C7a), 141.48 (C2), 139.07 (C12), 134.53 (C4a), 130.17 (C12a), 126.85 (C12b), 122.83 (C8), 108.53 (C11), 107.15 (C4), 61.43 (C1-OCH$_3$), 61.35 (C2-OCH$_3$), 56.09 (C3-OCH$_3$), 52.52 (C7), 49.03 (C4'), 45.48 (C2'), 45.13 (C6'), 37.28 (C3'), 37.20 (C6), 32.67 (C5'), 30.07 (C5), 22.94 (C14); HR-MS: m/z calcd 468.2448 for C$_{26}$H$_{33}$N$_3$O$_5$+H$^+$ (468.2493); IR (CHCl$_3$): ν$_{max}$ 3305, 2927, 2853, 2802, 1654, 1579, 1488, 1463, 1427, 1283, 1194, 1095, 1045 cm$^{-1}$.

Example 3: Synthesis of N-[(7S)-1,2,3-Trimethoxy-9-oxo-10-(N-boc-piperazin-1-yl)-5,6,7,9-tetrahydrobenzo[a]heptalen-7-yl]acetamide (1c)

Procedure for synthesis of 1c is similar to example 1 except corresponding amine (N-boc-Piperazine). Yield, 60%; yellow solid; mp 158-160° C. $^1$H NMR (MeOD, 500 MHz): δ 7.32 (1H, d, J=11.0 Hz, C12-H), 7.18 (1H, s, C8-H), 7.05 (1H, d, J=11.0 Hz, C11-H), 6.72 (1H, s, C4-H), 4.48-4.46 (1H, m, C7-H), 3.91-3.81 (2H, m, C2'-Ha, C6'-Ha), 3.89 (3H, s, Ar—OCH$_3$), 3.58 (3H, s, Ar—OCH$_3$), 3.45-3.42 (2H, m, C2'-Hb, C6'-Hb), 3.30 (3H, s, Ar—OCH$_3$), 2.65-2.57 (2H, m, C3'-Ha, C5'-Ha). 2.39-2.31 (2H, m, C3'-Hb, C5'-Hb), 2.20-2.12 (2H, m, C6-Ha, C5-Ha), 1.98 (3H, s, C14-CH$_3$), 1.95-1.94 (2H, m, C5-Hb, C6-Hb), 1.48 (9H, —CH$_3$×3); $^{13}$C NMR (CDCl$_3$, 125 MHz): δ 181.28 (C9), 169.43 (C13), 157.98 (C10), 154.73 (CT), 153.24 (C3), 151.37 (C1), 149.15 (C7a), 141.74 (C2), 135.93 (C12), 134.34 (C4a), 134.24 (C12a), 129.41 (C8), 125.96 (C12b), 118.03 (C11), 107.39 (C4), 80.07 (C8'), 61.40 (C1-OCH$_3$), 61.40 (C2-OCH$_3$), 56.13 (C3-OCH$_3$), 51.88 (C7), 48.53 (C2'), 48.53 (C6'), 37.24 (C6), 30.02 (C5), 29.70 (C3'), 29.70 (C5'), 28.45 (C9'), 28.45 (C10'), 28.45 (C11'), 22.69 (C14); HR-MS: m/z calcd 554.2885 for C$_{30}$H$_{39}$N$_3$O$_7$+H$^+$ (554.2861); IR (CHCl$_3$): ν$_{max}$ 3390, 2924, 2854, 1653, 1422, 1322, 1232, 1160, 1044 cm$^{-1}$.

Example 4: Synthesis of N-[(7S)-1,2,3-Timethoxy-9-oxo-10-(4-phenyl-piperidin-1-yl)-5,6,7,9-tetrahydrobenzo[a]heptalen-7-yl]acetamide (1d)

Procedure for synthesis of 1d is similar to example 1 except corresponding amine (4-Phenyl-piperidine). Yield, 78%; yellow solid; mp 169-172° C. $^1$H NMR (CDCl$_3$, 400 MHz): δ 7.35-7.31 (m, 3H, C9'-H, C10'-H, C11'-H) 7.28-7.20 (2H, C8'-H, C12'-H), 7.26 (1H, s, C8-H), 7.23 (1H, d, J=11.2 Hz, C12-H), 6.84 (1H, d, J=11.2 Hz, C11-H), 6.51 (1H, s, C4-H), 4.65-4.62 (1H, m, C7-H), 4.27-4.24 (1H, m, C2'-Ha), 4.11-4.08 (1H, m, C6'-Ha), 3.94 (3H, s, Ar—OCH$_3$), 3.89 (3H, s, Ar—OCH$_3$), 3.66 (3H, s, Ar—OCH$_3$), 3.06-3.05 (1H, m, C4'-H), 2.86-2.80 (2H, m, C2'-Hb, C6'-Hb), 2.48-2.42 (2H, m, C6-Ha, C5-Ha), 2.22-2.17 (1H, m, C6-Hb), 2.04 (3H, s, C14-CH$_3$), 2.03-1.92 (3H, m, C5-Hb, C3'-Ha, C5'-Ha). 1.85-1.84 (2H, m, C3'-Hb, C5'-Hb); $^{13}$C NMR (CDCl$_3$, 125 MHz): δ 181.51 (C9), 169.79 (C13), 158.62 (C10), 153.06 (C3), 151.31 (C1), 149.10 (C7a), 145.60 (C7'), 141.57 (C2), 136.19 (C12), 134.41 (C4a), 134.30 (C12a), 128.80 (C8), 128.86 (C9'), 128.86 (C11'), 126.86 (C8'), 126.86 (C12'), 128.41 (C10'), 126.11 (C12b), 118.03 (C11), 107.27 (C4), 61.47 (C1-OCH$_3$), 61.42 (C2-OCH$_3$), 56.09 (C3-OCH$_3$), 51.87 (C7), 49.76 (C2'), 49.68 (C6'), 42.84 (C3'), 36.99 (C6), 33.55 (C3'), 31.14 (C5'), 30.09 (C5), 23.05 (C14); HR-MS: m/z calcd 529.2696 for C$_{32}$H$_{36}$N$_2$O$_5$+H$^+$ (529.2697); IR (CHCl$_3$): ν$_{max}$ 3291, 2932, 2850, 1654, 1601, 1543, 1486, 1399, 1321, 1216, 1095, 1007 cm$^{-1}$.

Example 5: Synthesis of N-[(7S)-1,2,3-Trimethoxy-9-oxo-10-(L-prolinol-1-yl)-5,6,7,9-tetrahydrobenzo[a]heptalen-7-yl]acetamide (1e)

Procedure for synthesis of 1e is similar to example 1 except corresponding amine (L-Prolinol). Yield, 81%; yellow solid; mp 164-166° C. $^1$H NMR (CDCl$_3$, 500 MHz): δ 7.91 (1H, d, J=6.2 Hz, NH), 7.33 (1H, d, J=11.8 Hz, C12-H), 7.25 (1H, s, C8-H), 6.53 (1H, s, C4-H), 6.48 (1H, d, J=11.8 Hz, C11-H), 6.2 (1H, s, br, C5'-OH), 5.35-5.33 (1H, m, C3'-H), 4.55-4.53 (1H, m, C7-H), 3.93 (3H, s, Ar—OCH$_3$), 3.88 (3H, s, Ar—OCH$_3$), 3.73-3.69 (2H, m, C6'-H), 3.62 (3H, s, Ar—OCH$_3$), 3.55-3.52 (1H, m, C2'-Ha), 3.47-3.41 (1H, m, C5'-Ha), 2.44-2.42 (1H, m, C6-Ha), 2.34-2.25 (2H, m, C6-Hb, C5-Ha), 2.12-2.11 (2H, m, C2'-Hb, C5'-Hb), 2.01 (3H, s, C14-CH$_3$), 2.01-1.97 (2H, m, C4'-H), 1.97-1.87 (1H, m, C6-Hb); $^{13}$C NMR (CDCl$_3$, 125 MHz): δ 176.77 (C9), 169.85 (C13), 156.25 (C10), 152.92 (C3), 151.34 (C1), 149.89 (C7a), 141.49 (C2), 138.27 (C12), 134.69 (C4a), 129.65 (C12a), 126.20 (C12b), 123.54 (C8), 113.10 (C11), 107.35 (C4), 64.15 (C6'), 62.20 (C2'), 61.43 (C1-OCH$_3$), 61.27 (C2-OCH$_3$), 56.08 (C3-OCH$_3$), 52.04 (C7), 50.58 (C5'), 37.47 (C6), 30.15 (C5), 28.51 (C5'), 23.01 (C4'), 22.45 (C14); HR-MS: m/z calcd 469.2336 for C$_{26}$H$_{32}$N$_2$O$_6$+H$^+$ (469.2333); IR (CHCl$_3$): ν$_{max}$ 3350, 2928, 2853, 1653, 1598, 1527, 1486, 1455, 1401, 1382, 1349, 1237, 1145, 1096, 1019 cm$^{-1}$.

Example 6: Synthesis of N-[(7S)-1,2,3-Trimethoxy-9-oxo-10-(2,3,4,9-tetrahydro-1H-pyrido[3,4-b]indole-2-yl)-5,6,7,9-tetrahydrobenzo[a]heptalen-7-yl]acetamide (1f)

Procedure for synthesis of 1f is similar to example 1 except corresponding amine (Tryptoline). Yield, 62%; yellow solid; mp 158-160° C. $^1$H NMR (CD$_3$OD, 500 MHz): δ 7.44 (1H, d, J=10.0 Hz, C12-H), 7.35 (1H, d, J=10.0 Hz, C11-H), 7.30 (1H, m, C9'-H), 7.18 (1H, s, C8-H), 7.15-6.98 (2H, m, C10'-H, C11'-H), 6.75-6.73 (1H, m, C8'-H), 6.72 (1H, s, C4-H), 4.75-4.69 (1H, m, C7-H), 4.51-4.43 (1H, m, C6'-Ha), 4.10-4.01 (1H, m, C6'-Hb), 3.89 (3H, s, Ar—OCH$_3$), 3.87 (3H, s, Ar—OCH$_3$), 3.63-3.61 (1H, m, C2'-Ha), 3.57 (3H, s, Ar—OCH$_3$), 3.10-2.90 (2H, m, C2'-Hb, C3'-Ha), 2.61-2.51 (1H, m, C6-Ha), 2.45-2.25 (2H, m, C3'-Hb, C6-Hb), 2.24-2.10 (1H, m, C5-Ha), 1.99 (3H, s, C14-CH$_3$), 1.99-1.97 (1H, m, C5-Hb); $^{13}$C NMR (CD$_3$OD, 100 MHz): δ 171.65 (C9), 167.16 (C13), 159.69 (C10), 158.44 (C3), 154.83 (C1), 151.92 (C7a), 142.69 (C2), 138.47 (C12), 138.07 (C12'), 136.23 (C4a), 132.09 (C12a), 130.38 (C8), 128.83 (C7'), 128.32 (C12b), 127.26 (C5'), 122.16 (C9'), 120.47 (C4'), 119.86 (C10'), 118.60 (C8'), 116.20 (C11'), 111.92 (C11), 108.83 (C4), 61.67 (C1-OCH$_3$), 61.67 (C2-OCH$_3$), 56.65 (C3-OCH$_3$), 53.39 (C7), 48.66 (C2'), 44.54 (C6'), 37.71 (C6), 30.73 (C5), 22.50 (C3'), 22.45 (C14); HR-MS: m/z calcd 540.2493 for C$_{32}$H$_{33}$N$_3$O$_5$+H$^+$ (540.2493); IR (CHCl$_3$): ν$_{max}$ 3392, 2923, 2852, 1649, 1602, 1537, 1487, 1454, 1399, 1349, 1321, 1219, 1095, 1043, 1019 cm$^{-1}$.

Example 7: Synthesis of N-[(7S)-1,2,3-Trimethoxy-9-oxo-10-[3-(trifluoromethyl)-4-chloro-phenylamino]-5,6,7,9-tetrahydrobenzo[a]heptalen-7-yl] acetamide (1g)

Procedure for synthesis of 1g is similar to example 2 except corresponding amine (3-Trifluoromethyl-4-chlorophenylamine). Yield, 62%; yellow solid; mp 168-171° C. $^1$H NMR (CDCl$_3$, 500 MHz): δ 8.71 (1H, s, C10-NH), 7.66 (1H, s, C8-H), 7.59 (1H, d, J=4 Hz, C5'-H), 7.56 (1H, s, C2'-H), 7.50 (1H, d, J=4 Hz, C6'-H), 7.40 (1H, d, J=12.0 Hz, C12-H), 7.23 (1H, d, J=12.0 Hz, C11-H), 6.54 (1H, s, C4-H), 4.71-4.69 (1H, m, C7-H), 3.93 (3H, s, Ar—OCH$_3$), 3.90 (3H, s, Ar—OCH$_3$), 3.65 (3H, s, Ar—OCH$_3$), 2.54-2.51 (1H, m, C5-Ha), 2.44-2.29 (2H, m, C5-Hb, C6-Ha), 2.02 (3H, s, C14-CH$_3$) 1.94-1.92 (1H, m, C6-Hb); $^{13}$C NMR (CDCl$_3$, 100 MHz): δ 175.83 (C9), 169.73 (C13), 153.35 (C10), 152.14 (C3), 151.12 (C1), 150.79 (C7a), 141.58 (C2), 138.46 (C12), 137.40 (C3'), 134.53 (C1'), 134.26 (C4a), 132.79 (C8), 132.79 (C7'), 128.41 (C12a), 127.21 (C6'), 126.27 (C12b), 125.90 (C5'), 122.58 (C4'), 122.54 (C2'), 110.45 (C11), 107.27 (C4), 61.47 (C1-OCH$_3$), 61.41 (C2-OCH$_3$), 56.13 (C3-OCH$_3$), 52.70 (C7), 37.21 (C6), 29.97 (C5), 22.99 (C14); HR-MS: m/z calcd 563.1556 for C$_{28}$H$_{26}$ClF$_3$N$_2$O$_5$+H$^+$ (563.1555); IR (CHCl$_3$): ν$_{max}$ 3270, 3001, 2929, 2855, 1660, 1601, 1582, 1543, 1502, 1487, 1463, 1402, 1349, 1322, 1236, 1194, 1142, 1096, 1047, 1015 cm$^{-1}$.

Example 8: P-Gp Induction Assay

All synthesized compounds were screened for their ability to induce P-gp by using rhodamine123 (Rh123) cell exclusion method. In this method, the P-gp function was evaluated in terms of rhodamine 123 (Rh123) accumulation and efflux. Briefly, the protocol used is as follows: Colorectal LS-180 cells (ECACC type, purchased from Sigma, Cat. no. 87021202, cell passage no. 52) were seeded at a density of 2×10$^4$ per well of 96 well plate and were allowed to grow for next 24 h. Cells were further incubated with the test compounds, and were diluted to a final concentration of 100 nM and rifampicin (standard) to a final concentration of 10 μM in complete media for 48 h. The final concentration of DMSO was kept at 0.1%. Drugs were removed and cells were incubated with HANKS buffer for 40 minutes before further incubation with HANKS buffer (containing 10 μM of Rh123 as a P-gp substrate) for 90 minutes. At the end of Rh123 treatment cells were washed four times with cold PBS followed by cell lysis for 1 h by using 200 μl of lysis buffer (0.1% Triton X-100 and 0.2 N NaOH). A total of 100 μl of lysate was used for reading fluorescence of Rh123 at 485 nm/529 nm. Samples were normalized by dividing fluorescence of each sample with total protein present in the lysate. For $EC_{50}$ determination, different concentrations of compound were used to treat LS180 cells for 48 h. $EC_{50}$ was determined by plotting fluorescence of Rh123 against concentration of compound.

Colchicine showed potent P-gp induction activity as indicated by the decrease in % intracellular accumulation of Rh123 in LS180 cells (62%) compared to the control (100%). However, synthesized compounds displayed significantly reduced P-gp induction activity; which comprises of compounds substituted with Piperazine 1a, 4-Amino piperidine 1b, 4-Phenyl piperidine 1d, Tryptoline 1f, 4-Chloro-3-(trifluoromethyl)aniline 1g all showing 90% intracellular accumulation of Rh123 in LS180 cells compared to the control (100%) (FIG. 2). Further, the $EC_{50}$ values of selected compounds 1d and 1g along with colchicine (1) was calculated for P-gp induction activity. The derivative 1d and 1g showed higher $EC_{50}$ value compared to colchicine (1). These results suggest that synthesized compounds are less liable to P-gp induction compared to colchicine (1) (Table 1).

TABLE 1

Induction of P-gp in P-gp overexpressing LS-180 cells using rhodamine 123 (Rh 123) cell exclusion method

| Entry | $EC_{50}$ (nM) |
|---|---|
| 1 | 14.4 |
| 1d | 29.6 |
| 1g | 69 |

Example 9. Antiproliferative Activity

Human colon cancer cell lines HCT-116 (NCI, passage no. 5) and Colo-205 116 (NCI, passage no. 3) were procured from National Cancer Institute, USA. HCT-116 and Colo-205 cells were grown in McCoy's 5A and RPMI growth medium respectively containing 10% FCS, 100 U penicillin and 100 mg streptomycin per mL medium. Cells were grown in $CO_2$ incubator (Thermocon Electron Corporation, Houston, Tex.) at 37° C. with 95% humidity and 5% $CO_2$ gas environment. Cells treated with tested materials were dissolved in DMSO while the untreated control cultures received only the vehicle (DMSO<0.2%). Cells were seeded in 96 well plates and exposed to tested compounds at various concentrations for 48 h time interval. MTT dye (2.5 mg/ml in PBS) was added 4 hrs priors to experiment termination. The plates were then centrifuged at 1500 rpm for 15 min and the supernatant was discarded, and MTT formazan crystals were dissolved in 150 μl of DMSO. The OD measured at 570 nm with reference wavelength of 620 nm.

The percentages of cell viability and growth inhibition were calculated using formulas:

The % of cell viability =

$$\frac{\text{Absorbance of treated cells} - \text{Absorbance of Blank}}{\text{Absorbance of control cells} - \text{Absorbance of Blank}} \times 100$$

% Growth inhibition = 100 − % of cell viability

The results are summarized in Table 2. The 10-amino substituted compound 1g displayed promising antiproliferative activity in both cell lines (HCT-116, Colo-205) with $IC_{50}$ values of 0.040 and 0.030 μM, respectively. The compound 1g showed better antiproliferative activity compared to natural product colchicine. The compounds exhibiting promising cytotoxicity in HCT-116 cells ($IC_{50} \leq 1$ μM) along with complete loss of P-gp induction activity include 1g, and 1d.

TABLE 2

Antiproliferative activities of colchicine and synthisized compounds (1a-1g)

| Entry | R | HCT-116 ($IC_{50}$, μM) | Colo-205 ($IC_{50}$, μM) |
|---|---|---|---|
| 1 | (Colchicine as standard-$OCH_3$ control) | 0.050 | 0.032 |
| 1a | piperazine (HN-N-) | >10 | 8.0 |
| 1b | 4-aminopiperidine ($H_2N$-piperidine-N-) | 10 | 5.0 |
| 1c | Boc-piperazine | 4.0 | 3.0 |
| 1d | 4-phenylpiperidine | 1.0 | 0.8 |
| 1e | prolinol | 10 | 8.0 |
| 1f | tryptoline | 3.0 | 0.8 |
| 1g | 4-Chloro-3-(trifluoromethyl)aniline (Cl, $F_3C$-C$_6$H$_3$-NH-) | 0.040 | 0.030 |

Example 10. Effect of Compounds on Microtubules

For detection of tubulins, HCT-116 cells (1×10$^5$ cells/well) were seeded on to 18 mm square cover slips in six well plates in complete medium. Cells were allowed to adhere for 24 h and were treated with respective concentrations of compounds 1, 1d and 1g for 24 h. After the treatment period, cells were fixed in 4% paraformaldehyde for 10 min at room temperature and permeabilized using 0.5% Triton-X in PBS for 5 min. The cells were blocked with 10% goat serum for 20 min at room temperature. Microtubules were detected with a monoclonal α-tubulin antibody (Sigma, Catalogue number: T9026) diluted 1:100 in 0.1% Triton X-100 in PBS for 1 h at room temperature and Alexa Fluor 488 conjugated secondary antibody (Invitrogen) diluted 1:500 in PBS for 1 h at room temperature. Cells were then washed three times in PBS and stained with 4',6-diamidino-2-phenylindole (DAPI 1 μg/ml in PBS). The cover slips were mounted over glass slides and cells were imaged by a laser scanning confocal microscope (Olympus Fluoview FV1000). The promising candidates identified through P-gp screening and antiproliferative screening were further studied for tubulin polymerization inhibition activity. Colchicine (1), 10-amino linked derivative 1d and 1g were tested for their ability to show disruption of microtubule assembly using confocal microscopy. As shown in FIG. 3, the cells treated with colchicine (1), derivative 1d and 1g showed a remarkable disruption and loss of microtubules compared to the control.

Example 11. Determination of Thermodynamic Equilibrium Solubility

The compounds were first dissolved in methanol to prepare stock solutions (100 and 1000 μg/mL). Different concentrations of stock solutions were pipetted into the 96-well plates and the solvent was evaporated to ensure that solid drug was present in the beginning of the experiment. Thereafter, 200 μl of the dissolution medium was added to the wells and 96-well plate was shaken horizontally at 300 rpm (Eppendorf Thermoblock Adapter, North America) for 4 h at room temperature (25±1° C.). The plates were kept overnight for equilibration of drug in medium. Later, the plates were centrifuged at 3000 rpm for 15 min (Jouan centrifuge BR4i). Supernatant (50 μl) was pipetted into UV 96-well plates (Corning® 96 Well Clear Flat Bottom UV-Transparent Microplate) for analyses with plate reader (SpectraMax Plus384) at $\lambda_{max}$ of 350 nm. The analyses were performed in triplicate for each compound. The solubility curve of concentration (μg/mL) vs absorbance was plotted to find out saturation point and the corresponding concentration was noted.

The solubility of colchicine (1) and best compounds 1d and 1g were determined in biological medias such as phosphate buffer saline (PBS), simulated gastric fluid (SGF), and simulated intestinal fluid (SIF). Results are shown in Table 3.

TABLE 3

Solubility of compounds 1, 1d and 1g in water, PBS, SGF and SIF

| Compound | Solubility in μg/mL | | | |
| --- | --- | --- | --- | --- |
|  | Water | PBS | SGF | SIF |
| 1 | >1500 | 800 | 200 | 800 |
| 1d | 80 | 80 | >1500 | 20 |
| 1g | >1500 | >1500 | >1500 | >1500 |

Example 12. Pharmacokinetic Studies

Oral and intravenous (IV) pharmacokinetic studies of compound 1g were carried out in BALB/c male mice (Jubilant Biosys Limited, Bangalore) of age 4-6 weeks, by administering 1g orally and IV at dose of 10 mg/kg for oral and 1 mg/kg for IV. Plasma samples were collected at appropriate time points between the range of 0 hours to 24 hours and analyzed by LC-MS-MS. Mean plasma concentration calculated and data were further analyzed for PK parameters using WinNonlin 5.3 software package. Following oral administration, elimination half life ($t_{1/2,\beta}$) was found to be 5.43 h and $AUC_{0-t}$ was found to be 16899 ng·h/mL. Following IV administration, elimination half life ($t_{1/2,\beta}$) was found to be 2.78 h and clearance was ~6 mL/min/Kg. The absolute oral bioavailability was 64%. The pharmacokinetic parameters are summarized in Table 4 and 5.

TABLE 4

Pharmacokinetic parameters of compound 1g post PO dose at 10 mg/Kg to BALB/c mice.

| Parameter | Unit | Value |
| --- | --- | --- |
| $t_{1/2,\beta}$ | (h) | 5.43 |
| $AUC_{0-t}$ | (ng · h/mL) | 16899 |
| $AUC_{0-\infty}$ | (ng · h/mL) | 17334 |
| $C_{max}$ | (ng/mL) | 3031 |
| $t_{max}$ | (h) | 2.00 |
| Bioavailability | (% F) | 64.4 |
| Time points considered for $t_{1/2,\ \beta}$ calculation: | | 8-24 h |

TABLE 5

Pharmacokinetic parameters of compound 1g post IV dose at 1 mg/Kg to BALB/c mice.

| Parameter | Unit | Value |
| --- | --- | --- |
| $t_{1/2,\ \beta}$ | (h) | 2.78 |
| $C_{max}$ | (ng/mL) | 698 |
| $C_0$ | (ng/mL) | 819 |
| $AUC_{0-t}$ | (ng · h/mL) | 2343 |
| $AUC_{0-\infty}$ | (ng · h/mL) | 2691 |
| CL | (mL/min/Kg) | 6.19 |
| $V_d$ | (L/Kg) | 1.49 |
| $V_{dss}$ | (L/Kg) | 1.47 |
| $T_{last}$ | (h) | 8.00 |
| Time points considered for $t_{1/2,\ \beta}$ calculation | | 2-8 h |

$C_0$ calculated manually using initial 3 time points
$t_{1/2,\beta}$: terminal half life;
$AUC_{0-t}$: the area under the plasma concentration-time curve from 0 to last measurable time point;
$AUC_{0-\infty}$: area under the plasma concentration-time curve from time zero to infinity;
$C_{max}$: maximum observed plasma concentration;
$C_0$: extrapolated concentration at zero time point;
CL: clearance;
$V_d$: volume of distribution;
$V_{dss}$: volume of distribution at steady state;
$T_{last}$: time at which last concentration was found;
F: bioavailability.

Example 13. In Vivo Activity in Ehrlich Solid Tumor Model

Ehrlich ascites carcinoma (EAC) cells were collected from the peritoneal cavity of the swiss mice (animal house of IIIM registered eith CPCSEA; registration no. 67/99/CPCSEA) weighing 18-23 gm, harbouring 8-10 days old ascitic tumor. 1×10$^7$ EAC cells were injected intramuscularly in the right thigh of 38 swiss male mice selected for the experiment on day 0. The next day, animals were randomized and divided into five groups. Four treatment groups contained 7 animals each and one control group contained 10 animals. Treatment was given as follows:

Group I: 1 (0.75 mg/kg, i/p) from day 1-9.
Group II: 1g (1 mg/kg, i/p) from day 1-9.

The third treatment group was treated with 5-fluorouracil (22 mg/kg, i/p) from day 1-9 and it served as positive control. The control group was similarly administered normal saline (0.2 ml, i/p) from day 1-9. On day 9 & 13, tumor bearing thigh of each animal was shaved and longest and shortest diameters of the tumor were measured with the help of vernier caliper. Tumor weight of each animal was calculated using the following formula.

$$\text{Tumor weight (mg)} = \frac{\text{Length (mm)} \times [\text{width (mm)}]^2}{2}$$

The percent tumor growth inhibition was calculated on day 13 by comparing the average values of treated groups with that of control group. Tumor growth in saline treated control animals was taken to be 100%.

The results are summarized in Table 6. The compound 1g has shown promising activity at 1 mg/kg dose with 47.35% inhibition in tumor size compared to control. There is no mortality observed in the group treated with 4o. On the other hand, colchicine (1) has shown promising activity with 52.29% inhibition at 0.75 mg/kg dose but the mortality was observed in 2 animals in the group of 7 animals. However, colchicine (1) has shown toxicity at 1 mg/kg with mortality of 5 animals in the group of 7 animals. 5-Fluorouracil was used as positive control with 54.78% inhibition at dose 22 mg/kg. These results clearly indicate that our compound 1g has better safety profile compared to colchicine.

TABLE 6

In vivo activity of 1 and 1g in Ehrlich solid tumor model

| Treatment Groups | Avg. body weights (g) of animal on days | | | Day 13 | | % Tumor Growth Inhibition | Mortality |
|---|---|---|---|---|---|---|---|
| | 1 | 5 | 9 | Avg. body weights (g) | Avg. tumor weights (mg) | | |
| 1 (Colchicine, standard control; 0.75 mg/kg, i/p) | 22.28 | 21.42 | 20.2 | 19.25 | 705.0 | 52.29 | 2/7 |
| 1 (1 mg/kg, i/p)* | Nd | Nd | Nd | Nd | Nd | Nd | 5/7 |
| 1g (1 mg/kg, i/p) | 22.28 | 22.0 | 21.28 | 21.66 | 778.0 | 47.35 | 0/7 |
| 5-Fluorouracil (Positive control; 22 mg/kg, i/p) | 22.42 | 22.28 | 19.4 | 19.4 | 668.2 | 54.78 | 0/7 |
| Normal Control NS (0.2 ml, i/p) | 23.4 | 24.4 | 25.4 | 25.33 | 1477.94 | — | 0/10 |

*Colchicine (1) was toxic at 1 mg/kg with mortality of 5 animals in the group of 7 animals, therefore the tumor growth inhibition could not be determined.

Advantages of the Invention

The main advantages of the present invention are:
Compounds of the invention showed better antiproliferative activity, both in vitro as well as in vivo than natural product colchicine.
Compounds of the invention have significantly reduced P-gp substrate and induction liability compared to natural product colchicine.
Compounds of the invention have better solubility in biological fluids PBS, SGF and SIF compared to natural product colchicine.

Compounds of invention are not toxic as compared to natural product colchicine.

We claim:

1. A 10-substituted colchicinoid compound represented by the formula 1g

2. A process for the preparation of the compound of formula 1g as claimed in claim 1, wherein the compound is prepared by reacting colchicine (1) in polar organic solvent with 4-chloro-3-(trifluoromethyl)phenylamine in the ratio in the range of 1:4 under stirring at room temperature for 24-72 hours and purification by conventional method to obtain the compound of formula 1g.

3. A process as claimed in claim 2, wherein the polar organic solvent is selected from the group consisting of methanol, acetone, ethanol, dimethyl sulfoxide, ethyl acetate, and dimethylformamide.

4. A process as claimed in claim 2, wherein the temperature is preferably in the range of 25-40° C.

5. A process as claimed in claim 2, wherein the time period is preferably 60-70 hours.

6. A method of treating P-gp mediated multi-drug resistant cancer comprising administering a therapeutically effective amount of a 10-substituted colchicinoid compound as claimed in claim 1.

7. The compound as claimed in claim 1 for use in treatment of P-gp mediated multi-drug resistant cancer.

* * * * *